United States Patent [19]

Dahms

[11] Patent Number: 5,389,545
[45] Date of Patent: Feb. 14, 1995

[54] REAGENTS, METHODS AND KITS FOR WATER DETERMINATION

[76] Inventor: Harald Dahms, 472 Madison Ave., Toms River, N.J. 08753

[21] Appl. No.: 97,110

[22] Filed: Jul. 26, 1993

[51] Int. Cl.6 .......................................... G01N 33/18
[52] U.S. Cl. ...................................... 436/42; 436/39; 422/61
[58] Field of Search ........................ 436/8, 39, 42, 163, 436/111, 122, 125; 422/61

[56] References Cited

U.S. PATENT DOCUMENTS

| | | | |
|---|---|---|---|
| 2,780,601 | 2/1957 | Blomgren et al. | 436/42 |
| 2,967,155 | 1/1961 | Blomgren et al. | 436/42 |
| 3,656,907 | 4/1972 | Delmonte | 436/42 |
| 4,005,983 | 2/1977 | Dahms | 436/42 |
| 4,295,990 | 10/1981 | Verbeek et al. | 436/42 |
| 4,351,744 | 9/1982 | Muroi et al. | 436/42 |
| 4,354,853 | 10/1982 | Dahms | 436/42 |
| 4,550,083 | 10/1985 | Fischer et al. | 436/42 |
| 4,647,542 | 3/1987 | Fischer et al. | 436/42 |
| 4,703,014 | 10/1987 | Fischer et al. | 436/42 |
| 4,725,552 | 2/1988 | Dahms | 436/42 |
| 4,748,126 | 5/1988 | Fischer et al. | 436/42 |
| 4,789,638 | 12/1988 | Kramer et al. | 436/111 |
| 4,802,957 | 2/1989 | Kuwata et al. | 436/42 X |
| 5,102,804 | 4/1992 | Fischer et al. | 436/42 |
| 5,139,955 | 8/1992 | Scholz | 436/42 |
| 5,179,024 | 1/1993 | Dahms | 436/42 |
| 5,187,101 | 2/1993 | Kato et al. | 436/42 |

FOREIGN PATENT DOCUMENTS

| | | | |
|---|---|---|---|
| 1174951 | 9/1984 | Canada | 436/42 |
| 0484622 | 5/1992 | European Pat. Off. | 436/42 |
| 2176294 | 12/1986 | United Kingdom | 436/42 |
| 2234066 | 1/1991 | United Kingdom | 436/42 |

*Primary Examiner*—Jeffrey R. Snay
*Assistant Examiner*—Maureen M. Wallenhorst

[57] ABSTRACT

An essentially iodine-free and pyridine-free single component reagent for volumetric water analysis using the Karl Fischer reaction, a process for making the reagent, and the use of the reagent to determine the water content of a sample. The reagent contains triiodide ions as an oxidizing agent, a buffer such as an amine, a reducing agent such as $SO_2$, and a solvent. The presence of iodine, if any, is in an amount less than 1% of the amount of the triiodide ions.

38 Claims, No Drawings

REAGENTS, METHODS AND KITS FOR WATER DETERMINATION

DESCRIPTION

1. Field of the Invention

This invention relates to improved one-component reagents for water determination using the Karl Fischer reaction, and more particularly to volumetric one-component, pyridine-free reagents which are essentially iodine-free, containing triiodide, a reducing agent such as $SO_2$, a buffer such as an amide, and a solvent.

2. Background Art

The determination of moisture in materials such as liquids and solids by the Karl Fischer reaction is well known and widely used since it was first described by Karl Fischer in Angewandte Chemie 48, pages 394–396 (1935). Numerous publications have also described this technique for water determination, and reference is made to a general text by J. Mitchell, Jr. and D. M. Smith, entitled "Aquametry", published by John Wiley and Sons, 1980. Reference is also made to a publication by E. Scholz entitled "Karl Fischer Titration", published by Springer Verlag in 1984.

In a Karl Fischer reaction, the water to be determined reacts with iodine on a quantitative basis and consequently, the amount of reacted iodine is a measure of the amount of water present in the sample. The reaction proceeds according to the following expression:

(1) $H_2O + SO_2 + I_2 = 2H^+ + 2I^- + SO_3$

KF reagents are used in several types of analysis. A volumetric analysis using a volumetric reagent determines moisture by measuring the volume of the Karl Fischer reagent consumed during the analysis. A coulometric analysis using a coulometric reagent generates iodine by passing a current through the reagent and determines the moisture from the amount of current.

Karl Fischer reagents are divided into two groups, single-component and two-component systems. In the single-component systems, all ingredients (iodine, buffer, $SO_2$, and solvent) are in one solution. In the two-component systems, the "vessel" solution contains the buffer, $SO_2$, and a solvent, while the "titrant" solution contains iodine in a suitable solvent.

Both types of systems, one-component and two-component, have their advantages. The one-component reagents are more economical for users because they have to buy only one solution. However, there are disadvantages, particularly with respect to stability and shelf life. As soon as iodine, $SO_2$ and amine buffers are combined in the same solution they slowly react with each other. This reaction decreases the iodine level and therefore reduces the titer strength. This in turn limits the stability and shelf life of the reagent. This complication (which does not exist in two-component reagents) requires that the type of amine and the ratio of amine to $SO_2$ have to be carefully controlled to furnish good one-component reagents.

This stability problem has been recognized by Blomgren et al in U.S. Pat. Nos. 2,780,601 and 2,967,155, both of which describe pyridine based reagents. In the former, a suitable concentration of iodide ions was added as a stabilizing agent to reduce the speed of the spontaneous titer decrease so that the titer of the reagent will be less affected by the aforementioned spontaneous side reactions. However, it was found that the problem persisted even in reagents containing iodide ions as stabilizing agents. Therefore, the invention of U.S. Pat. No. 2,967,155 was directed to the use of a stabilizing base in the reagent, where the base strength of the stabilizing additive was chosen to be greater than that of the accelerating base (pyridine) used in these reagents. Generally, the use of pyridine is to be avoided due to odor and health problems, as well as its inferior performance characteristics.

U.S. Pat. No. 5,102,804 describes a modified Karl Fischer reagent for the determination of water which contains another iodine source instead of iodine. This source is an iodine halide or a mixture of this halide and a slat of an aromatic nitrogen containing heterocyclic compound. Advantages are stated to be that of increased stability and quicker reaction times.

While the prior art has provided some solutions to the problem of shelf life in one-component Karl Fischer reactions, it is desirable to provide one-component volumetric reagents which exhibit improved accuracy in addition to enhanced shelf life. This has been accomplished in the present invention wherein essentially iodine-free one-component reagents are described where the oxidizing reagent is triiodide that is present in the species as the triiodide ion $I_3$.

Accordingly, it is an object of this invention to provide an essentially iodine-free one-component volumetric reagent for the Karl Fischer determination of water content, where the oxidizing species is triiodide.

It is another object of this invention to provide an improved process for the volumetric determination of water in a sample using the Karl Fischer reaction, in which the one-component reagent that is employed contains triiodide, a buffer, $SO_2$, and a solvent.

It is another object of this invention to provide an improved pyridine-free, essentially iodine-free, one-component volumetric reagent, a method for making this reagent, and a method for using this reagent to determine water content, wherein improved accuracy results.

It is another object of this invention to provide an improved one-component Karl Fischer reagent containing triiodide, $SO_2$, a buffer, and a solvent wherein any iodine present in said reagent is present in an amount less than 1% of the amount of triiodide.

It is an object of this invention to provide an essentially iodine-free, pyridine-free volumetric Karl Fischer reagent containing triiodide as an oxidizing agent, a reducing agent, a buffer and a solvent.

It is another object of this invention to provide a process for water determination using the reagents described in the preceding objects.

BRIEF SUMMARY OF THE INVENTION

This invention relates to improved one-component volumetric reagents for use in determining the water content of a sample using the Karl Fischer reaction, methods for making these reagents, a process of water determination using these reagents and a kit which can be used to determine water content. The reagents are pyridine-free and essentially iodine-free, and contain triiodide as an oxidizing agent, a reducing agent such as $SO_2$, a buffer such as an amine to maintain a constant pH, and a suitable solvent. In these reagents, the dominant oxidizing agent is triiodide, and any iodine which may be present is present in an amount less than 1% of the amount of triiodide. The term "essentially iodine-free" will be described in considerably more detail later in this specification.

In use, a known amount of this reagent is added to a reaction cell containing a solvent in order to titrate to a first endpoint (thereby removing any water from the solvent). The sample is then dissolved in the solvent and the reagent is again added, to have titration to the same endpoint. The endpoints are typically indicated visually or through electronic circuitry. Since the titer of the reagent had been previously determined by means of a known quantity of water and since the volume of the added reagent is known, the water content of the sample can be calculated.

These and other objects, features, and advantages will be apparent from the following more particular description of the preferred embodiments.

DETAILED DESCRIPTION OF THE PREFERRED EMBODIMENTS

The reagents of this invention are pyridine-free single component volumetric reagents that are essentially iodine-free, and contain triiodide as an oxidizing agent. The reagents also contain a reducing agent such as $SO_2$, a buffer such as an amine, and a solvent.

In addition to the basic Karl Fischer reaction described above as equation 1, it is known that iodide ions can be added to a Karl Fischer reagent containing $SO_2$, a buffer such as an amine, and a solvent by adding water to the Karl Fischer reagent. The iodide ions combine with iodine according to the following expression:

(22) $I_2 + I = I_3$ 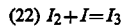

The species $I_3$ is the triiodide ion. Reaction 2 occurs in aqueous and in methanolic solutions, as well as in other solutions.

The reaction given by Equation 2 can be used to make the improved reagents of this invention since the reaction is driven predominantly to the right hand side of the equation, i.e., to $I_3$. As an example, in a first step a buffer (amine) and water are dissolved in a suitable solvent to produce a solution. Sulphur dioxide is then dissolved in the solution. Following this, iodine is added and dissolved by stirring the solution. The presence of water creates the iodide ions which then combine with iodine in accordance with Equation 2 to make the triiodide ions. By driving the equilibrium of this reaction toward $I_3$, triiodide will be formed and the solution will be essentially iodine-free. This is in contrast with reagents of the prior art where $SO_2$, an amine and iodine are dissolved in a suitable solvent and only very small amounts, if any, of $I_3$ are produced. In the present invention, sufficient water is present so that (essentially) all of the iodine is converted to triiodide in accordance with Equations 1 and 2. This will be explained in more detail by reference to the following examples which are merely illustrative and not limitative of the invention.

EXAMPLE 1

In the preparation of a pyridine-free, essentially iodine-free single component reagent, 136 grams (2 moles) of imidazole and 3.4 grams (0.19 moles) of water were dissolved in one liter of ethylene glycol monomethyl ether. After this, 96 grams (1.5 moles) of sulphur dioxide $SO_2$ were dissolved in the solution. Then 113 grams (0.445 moles) of iodine were dissolved in the solution by stirring. The 0.19 moles of water will react with 0.19 moles of iodine in accordance with Equation 1 and will form 0.38 moles of iodide ($I^-$), leaving 0.255 moles of iodine. This 0.255 moles of iodine will react with the 0.38 moles of iodide according to Equation 2 to produce a final reagent solution containing 0.255 moles of triiodide, and essentially no iodine.

EXAMPLE 2

This one-component reagent was made by dissolving 200 grams (1.9 moles) diethanolamine and 96 grams (1.5 moles) of sulphur dioxide and 3.6 grams (0.2 moles) of water in one liter of methanol. After this 140 grams (0.55 moles) of iodine are added and dissolved in the solution by stirring it. As with Example 1, and in accordance with the reactions given by Equations 1 and 2, triiodide is produced and the resultant reagent is essentially iodine-free.

EXAMPLE 3

This one-component reagent was prepared by dissolving 188 grams (2 moles) of n-propylamine, 102 grams (1.6 moles) sulphur dioxide, and 4.0 grams (0.22 moles) of water in one liter of ethyleneglycolmonomethyl ether. After this, 152 grams (0.6 moles) of iodine were added and dissolved into solution by stirring. As in Example 1, the reactions described in Equations 1 and 2 then occur to produce an essentially iodine-free reagent wherein the oxidizing agent is triiodide.

EXAMPLE 4

This one-component volumetric reagent was prepared by dissolving 112 grams (0.25 mole) of imidazole triiodide, 83 grams (1.3 moles) of $SO_2$ and 119 grams (1.75 moles) imidazole in 1 liter of ethyleneglycolmonomethyl ether.

Application of Reagents

The reagents prepared in examples 1–4 were used as volumetric reagents in a commercial titration apparatus (Ericsen Instruments Corp. Cat. No. AQ100). Each moisture analysis used 50 ml of methanol in the titration vessel. The methanol was pretitrated to a first endpoint. Then 50 mgs. of water were added to the vessel and a second titration undertaken to an identical endpoint. Accurate reproducible results were obtained.

In all of these examples the amount of water is more than one third the amount of iodine on a molar basis. This means that the Karl Fischer reaction given by Equation 1 and the reaction given by Equation 2 will occur while a solution is being prepared. This will convert iodine into the triiodide ion so that the finished solutions contain no or essentially no iodine, the oxidizing agent being triiodide ions (there being a possible excess of $I^-$).

In the preparation of these improved reagents, it is preferable that the buffer sulphur dioxide, and water are present before adding the iodine. If the iodine were added before the water, the iodine may enter side reactions leading to an inferior reagent.

As soon as the ratio of iodine/iodide is equal to 1, practically all of the oxidizing species becomes $I_3$ (triiodide) because of the reaction in Equation 2. The best results are obtained as soon as the iodide amount is at least equal to the iodine amount, i.e., $I^-|I_2 \geq 1$. If this is so, the resulting solution will be essentially iodine-free.

As the iodide concentration is further increased, at a constant iodine concentration, it has been found that the best results are obtained when the iodide/iodine ratio is in the range of about 1–2.5. However, superior reagents are still obtained when this ratio is above 2.5.

It is recognized that presently used Karl Fischer reagents of the single component type may contain limited amounts of triiodide in addition to some iodide. This occurs because all solvents contain small amounts of water. Due to this, the reactions given in Equations 1 and 2 occur to a limited extent and therefore presently used reagents may contain some triiodide in addition to iodine. This relative amounts of triiodide and iodine in those prior art reagents are significantly different that those in the improved reagents of the present invention, however, as will be explained in more detail.

Several electrochemical experiments have been conducted to show that the KF reagents of this invention contain essentially only triiodide and no iodine. These experiments involved the measurement of the oxidation-reduction potential of the reagents. A platinum wire was inserted into the solutions and its voltage was measured against a reference cell. The solution contained a known amount of iodine but no iodide. Then iodide was added in known amounts while the voltage was measured. At the point where the amount of iodide added was equal to the amount of iodine ($I_2 + I^- = I^-_3$) the redox potential of the platinum wire dropped suddenly by about 200 millivolt. These results prove to an electrochemist skilled in the art that triiodide was formed because the voltage drop occurred at an iodine to iodide ratio of 1. The large size of the drop (200 millivolts) shows that the amount of iodine left after the reaction is much less than 1% of the original amount of iodine.

As noted, very small amounts of iodine may be present in the reagents of this invention, as is apparent of a review of Equation 2. The amount of iodine that is present will, however, be so small that the iodine is immaterial as a titration agent. The equilibrium constant K of Equation 2 is given by the following expression:

$$K = \frac{[I_3^-]}{[I_2][I^-]} \quad (3)$$

Typically, K is in the order of $10^4$–$10^6$ (moles$^{-1}$ liter) in these new KF reagents and at a minimum is at least $10^3$ (moles$^{-1}$ liter). It can be easily shown that under these conditions there is very little iodine present as shown as more iodide than iodine is added to the reagent. For example, if 1 mole iodine per liter is combined with 1.01 moles of iodide per liter, 1 mole of triiodide is formed and 0.01 mole of iodide is left over. Even if a low K of $10^4$ is assumed, when these numbers are put into Equation 3 it yields $I_2 = 10^{-2}$ moles per liter. In this example, worst case assumptions were made i.e., $K = 10^4$ and $I^- = 0.01$. In the more realistic case where $K = 10^5$, even for $I^- = 0.01$, $I_2$ is present in an amount $10^{-3}$ moles per liter.

These iodine concentrations of 0.01 and 0.001 moles per liter, respectively, are so low that they are far outside the range of present conventional volumetric reagents in which iodine is in the range of 0.05–0.33 moles per liter.

Practical present volumetric reagents contain 0.05–0.33 moles per liter of iodine. Since the new reagents have to contain an equal amount of triiodide that means that the most preferred range of triiodide is 0.05–0.33 moles of triiodide per liter. Since the new reagents can also be prepared somewhat stronger, the preferred triiodide range is 0.05–0.6 moles of triiodide per liter.

The buffers used in these new reagents are non-pyridine buffers and preferably are numerous types of amines. It has been found that imidazole and its derivatives give the best results. These derivatives are compounds that contain the imidazole ring and wherein the hydrogen of the imidazole is substituted by one or more aliphatic or aromatic groups. Good results have also been obtained with diethanol amines or other aliphatic amines such as triethylamine—in general, aliphatic amines can be used.

Suitable amine buffers, besides the most preferred imidazole, include aliphatic amines, primary, secondary, or tertiary amines optionally containing zero to three oxygen atoms. Examples include diethanolamine, ethanolamine, triethanolamine, diethylamine, triethylamine, diisopropylamine, tri-n-butylamine, ethylenediamine and the like. Mixtures of such amines can also be used. In addition to the above-mentioned types of amines, other suitable amines include dimethylaniline, diphenylamine and other equivalent amines. Diethanolamine is a preferred amine.

The suitable range of amine:$SO_2$ ratio depends on the kind of amine used. For weak amines such as imidazole, the ratio is 10:1–0.5:1. For strong amines such as diethanolamine, it is only 2:5:1–0.5:1.

The solvents used for these improved reagents can be chosen from those customarily used. For example, an anhydrous low molecular weight alcohol can be used, such as ethylene glycol-monomethyl ether. Another suitable solvent is methanol.

By far the most preferred reducing agent is $SO_2$. Other reducing agents are described by Delmonte in U.S. Pat. No. 3,656,907. An example is dimethylsulfoxide. $SO_2$ may alternatively be used in an admixture with an acid such as a carboxylic acid. Suitable acids include formic, oxalic, sulfuric, hydriodic, and acetic acid. The molar ratio of sulfur dioxide to acid is typically in the range from about 20:1 to 1:5, with the preferable range being about 2:1 to 1:2.

In practice, these improved pyridine-free, iodine-free one-component volumetric reagents are used in the same manner as are other one-component reagents. That is, the reagent is added in measured amounts to titrate to an endpoint identical to the beginning endpoint.

The improved reagents of this invention have surprisingly shown increased accuracy in comparison to reagents wherein the titration agent is iodine. A comparison experiment was carried out to compare the performance of the titration reagent of Example 1 with that of a conventional reagent. The composition of the conventional reagent was identical to that given in Example 1, except that no water was used in its formulation. Consequently, the comparison was between the new triiodide reagent and the conventional iodine reagent. Both solutions were used as titrants in a manual conventional titration apparatus to titrate a known amount of 50 milligrams of water in methanol. Ten titrations were performed with each solution, the accuracy being found as follows:

New reagent: 50 mg±0.9 mg. Accuracy 1.8%
Old reagent: 50 mg±2.1 mg. Accuracy 4.2%.

Other experiments relating to accuracy were carried out, yielding the same result: namely, that the new reagents containing triiodide and essentially no iodine were more accurate. This is a very desirable feature which can for example, provide increased efficiency in a manufacturing process where the degree of accuracy is critical.

In these improved, essentially iodine-free reagents, a range of triiodide of 0.03–1 mole per liter is useful. However, the preferred range of triiodide is 0.05–0.6 moles per liter. In order to convert substantially all of the iodine into triiodide during formulation of the reagent in accordance with equation (2), the water that is present prior to adding iodine should be present in an amount at least ⅓ of the amount of iodine on a molar basis.

These new reagents can be employed in kits that are sold to users for the determination of water content. An example is a sealed vial containing these new reagents, where the unknown sample can be introduced into the vial (as by breaking a seal).

While the invention has been described with respect to particular embodiments thereof, it will be apparent to those of skill in the art that variations can be made therein without departing from the spirit and scope of the invention. The scope of the invention is intended to be limited only by the issued claims thereof.

It is claimed:

1. A single component volumetric Karl Fischer reagent for determining water content in a substance, said reagent containing a trace amount of iodine, triiodide ions, a buffer, $SO_2$ and a solvent, the amount of iodine present in said reagent being less than 1% of the amount of triiodide ion in said reagent and the molar amount of $SO_2$ in said reagent being greater than the molar amount of triiodide ions in said reagent.

2. The reagent of claim 1, where said buffer is an amide selected from the group consisting of imidazole and its derivatives and aliphatic amines.

3. The reagent of claim 2, where the ratio of amine:$SO_2$ is in the range 10:1–0.5:1 when the amine is imidazole and its derivatives.

4. The reagent of claim 1, where said triiodide ion is present in an amount between about 0.05 moles per liter and 0.6 moles per liter.

5. In a method for determining the water content of a substance using a volumetric Karl Fischer analysis wherein water to be determined reacts with an oxidizing agent on a quantitative basis and consequently, the amount of reacted oxidizing agent is a measure of the amount of water present in said substance, the improvement comprising using the volumetric reagent of claim 1.

6. An essentially iodine-free, single component volumetric reagent for the Karl Fischer volumetric analysis of moisture containing a trace amount of iodine, triiodide ions in an amount greater than 0.03 moles per liter, a buffer selected from the group consisting of imidazole and its derivatives, $SO_2$ and a solvent, the amount of iodine in said reagent being less than 1% of the amount of triiodide ions and the molar amount of $SO_2$ in said reagent being greater than the molar amount of triiodide ions in said reagent.

7. The reagent of claim 6, where said solvent contains two or more carbon atoms.

8. The reagent of claim 6, where the amount of triiodide ions in said reagent is in the range 0.05–0.6 moles per liter.

9. The reagent of claim 8, where the amount of iodine in said reagent is less than $10^{-2}$ moles per liter.

10. In a method for determining the water content of a substance using volumetric Karl Fischer analysis wherein water to be determined reacts with an oxidizing agent on a quantitative basis and consequently, the amount of reacted oxidizing agent is a measure of the amount of water present in said substance, the improvement comprising using the single component volumetric reagent of claim 6.

11. A pyridine-free, single-component volumetric reagent for the volumetric analysis of moisture by the Karl Fischer reaction, said reagent containing triiodide ions as an oxidizing agent, iodine in an amount less than $10^{-2}$ moles per liter, $SO_2$, an amine and a solvent, the molar amount of $SO_2$ in said reagent being greater than the molar amount of triiodide ions in said reagent.

12. The reagent of claim 11, where said triiodide ions are present in an amount 0.05–0.6 moles per liter.

13. The reagent of claim 12, where the amount of iodine in said reagent is less than 1% the amount of triiodide ions in said reagent.

14. The reagent of claim 12, where said amine is selected from the group consisting of imidazole and its derivatives.

15. The reagent of claim 11, where the amount of iodine in said reagent is less than $10^{-3}$ moles per liter.

16. In a method for determining the water content of a sample using volumetric Karl Fischer analysis, wherein water to be determined reacts with an oxidizing agent on a quantitative basis and consequently, the amount of reacted oxidizing agent is a measure of the amount of water present in said sample, the improvement comprising using the single component volumetric reagent of claim 11.

17. A single component Karl Fischer reagent kit comprising a sealed vial containing an essentially iodine-free reagent including iodine in an amount less than $10^{-2}$ moles per liter, triiodide ions, $SO_2$, a buffer and a solvent, the molar amount of $SO_2$ in said reagent being greater than the molar amount of triiodide ions in said reagent.

18. The kit of claim 17, where the amount of iodine in said reagent is less than 1% of the amount of triiodide ions in said reagent.

19. A single component Karl Fischer reagent kit comprising a sealed vial containing an essentially iodine-free reagent, said reagent containing triiodide ions as an oxidizing agent, iodine in an amount less than $10^{-2}$ moles per liter, a buffer, a reducing agent and a solvent, the amount of iodine in said reagent being less than 1% of the amount of triiodide ions in said reagent, the molar amount of said reducing agent in said reagent being greater than the molar amount of triiodide ions in said reagent.

20. In a method for determining water content of a sample using a Karl Fischer reagent kit wherein water to be determined reacts with an oxidizing agent on a quantitative basis and consequently, the amount of reacted oxidizing agent is a measure of the amount of water present in said sample, the improvement comprising employing the kit of claim 19.

21. A single component essentially iodine-free volumetric reagent for the volumetric analysis of moisture content using the Karl Fischer reaction, said reagent containing triiodide ions as an oxidizing agent, iodine in an amount less than $10^{-2}$ moles per liter, a non-pyridine buffer, a reducing agent and a solvent, the amount of iodine in said reagent being less than 1% of the amount of triiodide ions in said reagent and the molar amount of said reducing agent being greater than the molar amount of triiodide ions in said reagent.

22. The reagent of claim 21, where said triiodide ions are present in said reagent in an amount between about 0.05 and 0.6 moles per liter.

23. In a method for determining the water content of a sample using volumetric Karl Fischer analysis wherein water to be determined reacts with an oxidizing agent on a quantitative basis and consequently, the amount of reacted oxidizing agent is a measure of the amount of water present in said sample, the improvement comprising employing the single component volumetric reagent of claim 21.

24. An iodine-free single component volumetric Karl Fischer reagent for determining water content in a substance, said reagent containing triiodide ions, a buffer, $SO_2$ and a solvent, the molar amount of $SO_2$ in said reagent being greater than the molar amount of triiodide ions in said reagent.

25. The reagent of claim 24 where said buffer is an amine selected from the group consisting of imidazole and its derivatives and aliphatic amines.

26. The reagent of claim 24, where said triiodide ion is present in said reagent in an amount between about 0.05 moles per liter and 0.6 moles per liter.

27. In a method for determining the water content of a substance using a volumetric Karl Fischer analysis wherein water to be determined reacts with an oxidizing agent on a quantitative basis and consequently, the amount of reacted oxidizing agent is a measure of the amount of water present in said substance, the improvement comprising using the volumetric reagent of claim 24.

28. A single component Karl Fischer reagent kit comprising a sealed vial containing an iodine-free reagent including triiodide ions, $SO_2$, a buffer and a solvent, the molar amount of $SO_2$ in said reagent being greater than the molar amount of triiodide ions in said reagent.

29. A Karl Fischer reagent kit comprising a sealed vial containing an iodine-free one component Karl Fischer reagent of triiodide ions as an oxidizing agent, a buffer, a reducing agent and a solvent in which the molar amount of reducing agent in said reagent is greater than the molar amount of triiodide ions in said reagent.

30. In a method for determining water content of a sample using a Karl Fischer reagent kit wherein water to be determined reacts with an oxidizing agent on a quantitative basis and consequently, the amount of reacted oxidizing agent is a measure of the amount of water present in said sample, the improvement comprising employing the kit of claim 29.

31. A single component iodine-free volumetric reagent for the volumetric analysis of moisture content using the Karl Fischer reaction, said reagent containing triiodide ions as an oxidizing agent, a non-pyridine buffer, a reducing agent and a solvent, the molar amount of said reducing agent in said reagent being greater than the molar amount of triiodide ions in said reagent.

32. The reagent of claim 31, where said triiodide ions are present in said reagent in an amount between about 0.05 and 0.6 moles per liter.

33. In a method for determining the water content of a sample using volumetric Karl Fischer analysis wherein water to be determined reacts with an oxidizing agent on a quantitative basis and consequently, the amount of reacted oxidizing agent is a measure of the amount of water present in said sample, the improvement comprising employing the single component volumetric reagent of claim 31.

34. The reagent of claim 1 where the amount of $SO_2$ in said reagent is at least three times the amount of triiodide in said reagent.

35. The reagent of claim 11, where the amount of $SO_2$ in said reagent is at least three times the amount of triiodide in said reagent.

36. The reagent kit of claim 17, where the amount of $SO_2$ in said reagent is at least three times the amount of triiodide in said reagent.

37. The reagent of claim 24, where the amount of $SO_2$ in said reagent is at least three times the amount of triiodide in said reagent.

38. The reagent kit of claim 28, where the amount of $SO_2$ in said reagent is at least three times the amount of triiodide in said reagent.

* * * * *